(12) United States Patent
Fei et al.

(10) Patent No.: US 8,877,344 B2
(45) Date of Patent: Nov. 4, 2014

(54) RADICALLY POLYMERIZABLE PHENOTHIAZINE MACROMONOMER FOR USE IN THE COATING OF MEDICAL DEVICES

(75) Inventors: Jiangfeng Fei, Sleepy Hollow, NY (US); Henry Arndt, Elkhart, IN (US); Steven Fowler, Hertfordshire (GB)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

(21) Appl. No.: 13/817,050

(22) PCT Filed: Sep. 23, 2011

(86) PCT No.: PCT/US2011/053027
§ 371 (c)(1),
(2), (4) Date: Feb. 14, 2013

(87) PCT Pub. No.: WO2012/040599
PCT Pub. Date: Mar. 29, 2012

(65) Prior Publication Data
US 2013/0143055 A1     Jun. 6, 2013

Related U.S. Application Data

(60) Provisional application No. 61/385,737, filed on Sep. 23, 2010.

(51) Int. Cl.
| | |
|---|---|
| B32B 27/30 | (2006.01) |
| C08F 28/06 | (2006.01) |
| C07D 279/18 | (2006.01) |
| C07D 279/20 | (2006.01) |

(52) U.S. Cl.
CPC ............ *C07D 279/20* (2013.01); *C07D 279/18* (2013.01)
USPC .......................................... 428/522; 526/257

(58) Field of Classification Search
None
See application file for complete search history.

(56) References Cited

U.S. PATENT DOCUMENTS

| | | |
|---|---|---|
| 5,264,092 A | 11/1993 | Skotheim et al. |
| 5,520,786 A | 5/1996 | Bloczynski et al. |

FOREIGN PATENT DOCUMENTS

| | | |
|---|---|---|
| EP | 1867732 A1 | 12/2007 |
| WO | 2010141359 A2 | 12/2010 |

OTHER PUBLICATIONS

International Search Report for Application No. PCT/US2011/053027 dated Feb. 17, 2012.

*Primary Examiner* — Sheeba Ahmed
(74) *Attorney, Agent, or Firm* — Lerner, David, Littenberg, Krumholz & Mentlik, LLP

(57) ABSTRACT

The present invention is directed to phenothiazine-based macromonomer compounds and methods of making the same.

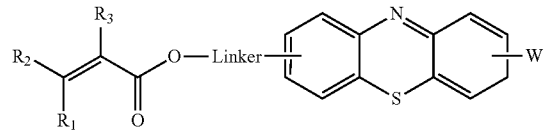

26 Claims, No Drawings

RADICALLY POLYMERIZABLE PHENOTHIAZINE MACROMONOMER FOR USE IN THE COATING OF MEDICAL DEVICES

CROSS-REFERENCE TO RELATED APPLICATIONS

The present application is a national phase entry under 35 U.S.C. §371 of International Application No. PCT/US2011/053027 filed on Sep. 23, 2011, published in English, which claims priority from U.S. Provisional Application Ser. No. 61/385,737 filed Sep. 23, 2010, all of which are incorporated herein by reference.

BACKGROUND OF THE INVENTION

U.S. Pat. No. 5,520,786 ('786) to Bloczynski et al. describes families of phenothiazine and phenoxazine compounds suitable for use as electron transfer mediators.

BRIEF SUMMARY OF THE INVENTION

One aspect of the present invention is directed to phenothiazine-based macromonomer compounds of Formula (I) and methods of making the same,

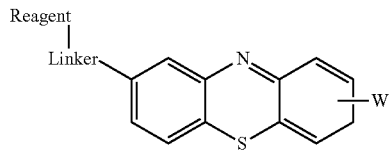
(I)

where the "linker" is an aliphatic group or PEG that is capable of reacting, binding, or trapping an enzyme or biological molecule;

W is selected from the group consisting of H, or a moiety derived from the group having the formula

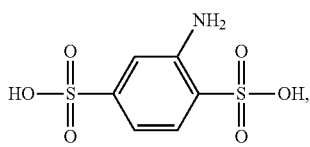 [SMILES: Nc1cc(S(=O)(=O)O)ccc1S(=O)(=O)O]

and the "reagent" is a moiety capable of undergoing further reaction, crosslinking, or polymerization with another molecule.

Another aspect of the present invention is directed to phenothiazine-based macromonomer compounds of Formula (Ia) and methods of making the same,

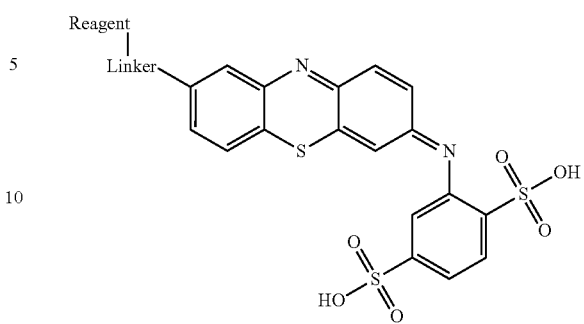
(Ia)

where the "linker" is an aliphatic group or PEG and is capable of reacting, binding, or trapping an enzyme or biological molecule; and the "reagent" is a moiety capable of undergoing further reaction, crosslinking, or polymerization with another molecule.

The present invention is also directed to reacting, crosslinking, or polymerizing the macromonomers of Formula (Ia) with each other or with other monomers, polymers, macromonomers. In some embodiments, homopolymers or heteropolymers are formed comprising monomers of the compounds of Formula (Ia). In other embodiments, homopolymers or heteropolymers are formed comprising monomers of the compounds of Formula (Ia) and other monomers, polymers, and macromonomers.

The present invention is further directed to forming films or layers of crosslinked or polymerized macromonomers of Formula (I). The present invention is yet further directed to applying the crosslinked or polymerized macromonomers of Formula (I) as a thin film on the surface of a transducer, electrode, or other device.

In some embodiments, the present invention is directed to changing the functionality of a phenothiazine, namely MLB (described further herein), such that it may be polymerized, such as by radical polymerization.

Without wishing to be bound by any particular theory, it is believed that by reacting, crosslinking or otherwise polymerizing the macromonomers of Formulas (I) or (Ia), it is possible to form a polymer, copolymer, gel, hydrogel, or viscous solution that can trap, bind, and/or react with enzymes and/or other biological molecules of interest, including flavin adenine dinucleotide ("FAD") and/or nicotinamide adenine dinucleotide ("NAD"). The invention also contemplates applying the formed polymer, copolymer, gel, hydrogel, or viscous solution, which may contain trapped, bound, or reacted biological material, as a film or layer on the surface of a device, transducer, or electrode. Also, the polymer, copolymer, gel, hydrogel, or viscous solution, which may contain trapped, bound, or reacted biological material may be grown or immobilized as a film or layer on the surface of a device, transducer, or electrode.

DETAILED DESCRIPTION

The present invention is directed to macromonomer compounds of Formulas (I) or (Ia) and methods of making the same,

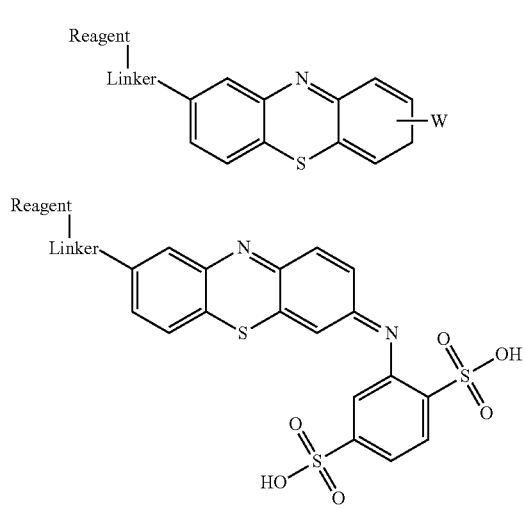

(I)

(Ia)

where the "linker" is an aliphatic group or PEG and is capable of reacting, binding, or trapping an enzyme or biological molecule;

W is selected from the group consisting of H, or a moiety derived from the group having the formula

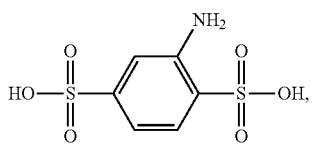 [SMILES: Nc1cc(S(=O)(=O)O)ccc1S(=O)(=O)O]

and the "reagent" is a moiety capable of, but not required to, undergo further reaction, crosslinking, or polymerization with another molecule.

Each of the components comprising Formulas (I) and (IIa) and its method of synthesis will be described in further detail herein.

The base moiety to which the linker is attached comprises a phenothiazine, a phenothiazine-precursor, or a phenothiazine-derivative (hereinafter "phenothiazine system"). In some embodiments phenothiazine systems, have the general structure shown in Formula (II):

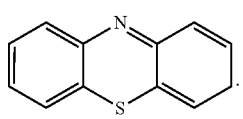

(II)

The compounds of Formula (II) may be derivatized at any position, such as at any ring carbon or heteroatom position. It is believed that such further derivatization may allow for additional crosslinking and/or polymer loading onto a substrate. The compounds of Formula (II) may be derivatized with groups including carboxylic acid groups and sulphonic acid groups any ring position, such as in Formula (IIa).

In one embodiment, the phenothiazine of Formulas (II) and (IIa) have the structure shown in Formula (III), namely (Z)-2-(3H-phenothiazin-3-ylideneamino)benzene-1,4-disulfonic:

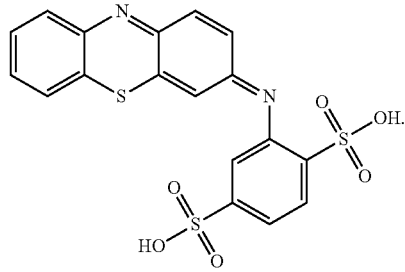

(III)

Of particular interest are those phenothiazine compounds of Formula (II) or Formula (III) that contain one or more linking moieties ("linker") such as in Formulas (IVa) and (IVb). The linker may be present at any ring position.

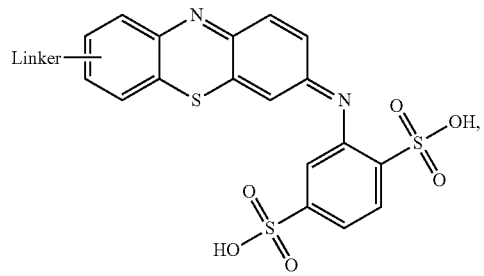

(IVa)

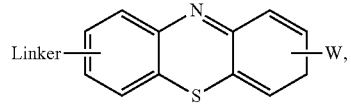

(IVb)

In some embodiments, the compounds of Formulas (IVa) and (IVb) have the structure shown in Formulas (IVc) and (IVd).

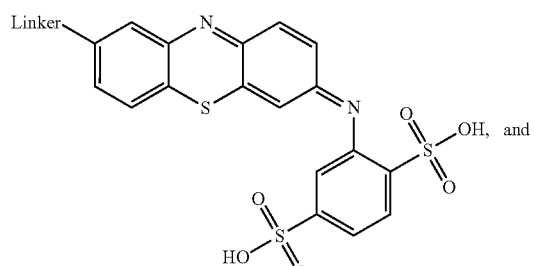

(IVc)

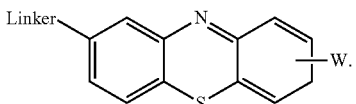

(IVd)

The linker may be any group capable of coupling a reagent ("reagent") molecule to the phenothiazine system. In some embodiments, the linker is a substituted or unsubstituted aliphatic group having between about 2 and about 12 carbon atoms. In other embodiments, the linker is a substituted or unsubstituted aliphatic group having between about 2 and about 8 carbon atoms. In yet other embodiments, the linker is a substituted or unsubstituted aliphatic group having between about 2 and about 4 carbon atoms. In some embodiments, the aliphatic group is substituted with halogen, alkoxy, or alkyl groups.

One skilled in the art will select a linker having an appropriate terminal functionality and/or leaving group for further reaction. In some embodiments, the terminal functional group and/or leaving group of the linker is a hydroxyl or halide group. In preferred embodiments, the linker has a terminal hydroxyl group.

In other embodiments, the phenothiazine-linker complex has the structure of Formulas (Va) or (Vb):

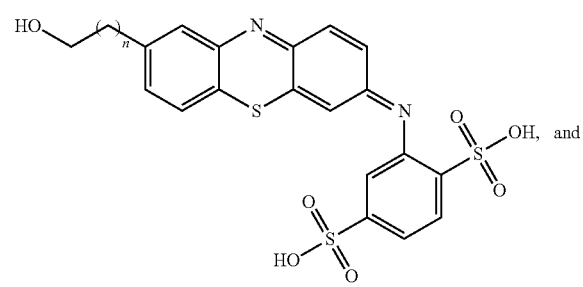

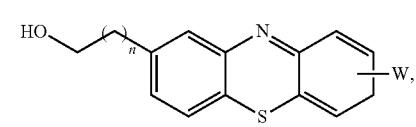

where n is an integer ranging from 1 to 12.

In yet other embodiments, the linker is derived from a polyethylene glycol molecule (hereinafter "PEG"). In its most common form, PEG is a linear polymer terminated at each end with hydroxyl groups: HO—CH$_2$CH$_2$O—(CH$_2$—CH$_2$O)$_n$—CH$_2$CH$_2$—OH, where n is a positive integer (more simply represented as HO-PEG-OH). In some embodiments, PEG is commonly used as an alkolxy-PEG-OH, in which one terminus is a relatively inert alkoxy group, while the other terminus is a hydroxyl group that is subject to ready chemical modification.

The compounds of Formulas (IVa), (IVb), (IVc), (IVd), (Va), and (Vb) are starting materials capable of reacting with a reagent as in Scheme 1 to form the macromonomer compounds of Formulas (I) and (Ia):

Scheme 1:
Reaction sequence showing the coupling of a reagent with the compounds of Formula (IVd) to form the compounds of Formula (Ic), which is a precursor to the macromonomers of Formula (Ia)).

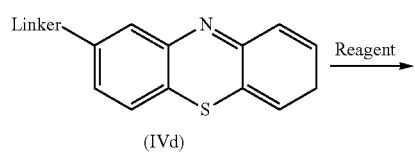

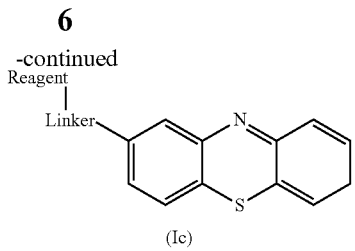

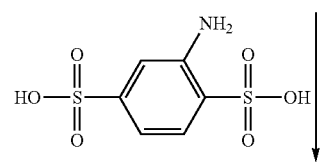

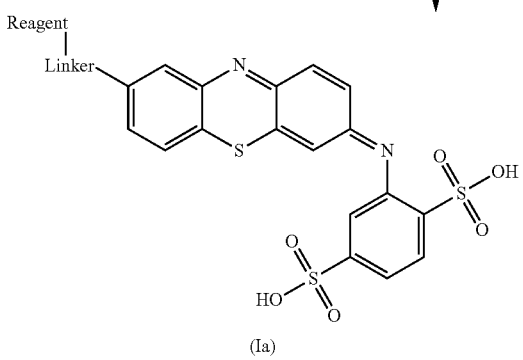

In other embodiments, the compounds of Formula (I) may be synthesized by directly coupling the compounds of Formula (IVa) or (IVc) with the appropriate reagent, such as when the group "W" is introduced after coupling of the reagent to the linker.

The coupling of the reagent to the linker may be accomplished by methods known to those skilled in the art, such as by nucleophillic substitution. Reaction conditions, acidic or basic depending on the reagent and/or linker functionality, are well known in the art. Any solvents typically used in substitution reactions can be used here, and one skilled in the art can select a solvent to provide the best yield and/or reactivity.

The reagent may be any molecule provided that it is capable of reacting with the linker to provide the macromonomer compounds of Formulas (I) or (Ia), or any appropriately derivatized analog thereof. In preferred embodiments, a reagent is selected such that it is capable of reacting, crosslinking, or polymerizing with another molecule including other macromonomers of Formulas (I) or (Ia) or with other monomers, polymers, macromonomers. In some embodiments, the reagent contains two functional groups. For example, the reagent may contain a carbonyl center (e.g. an ester or a acyl halide) and may also contain a vinyl group or another ethylenically unsaturated group. In these embodiments, and without wishing to be bound by any particular theory, it is believed that the carbonyl center reacts with functionality on the linker, leaving the vinyl group or other ethylenically unsaturated group available for further reaction, crosslinking, or polymerization with other molecules. In some embodiments, the reagent has the Formula (VI),

where Y is O—R, F, Cl, Br, or I;

R is H or a lower alkyl group having between 1 and 4 carbon atoms; and

Z is a substituted or unsubstituted aliphatic group having between about 2 and about 8 carbon atoms and comprising at least one vinyl group or ethylenically unsaturated group.

In some embodiments, Z is an aliphatic group having between about 2 and about 6 carbon atoms and at least one vinyl group or other ethylenically unsaturated group. In other embodiments, Z is an aliphatic group having between about 2 and about 4 carbon atoms and at least one vinyl group or other ethylenically unsaturated group. In any of these embodiments, the vinyl group or other ethylenically unsaturated group may be within the aliphatic chain or at a terminal position and may further have any stereochemical conformation (E, Z, cis, trans).

In some embodiments, the compounds of Formula (VI) are the various acrylates, methacrylates, or ethylenically unsaturated reagents known to those skilled in the art.

In some embodiments, the reagent has the Formula (VII),

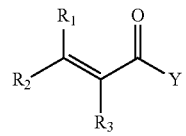

(VII)

where Y is O—R, F, Cl, Br, or I;

R is H or a lower alkyl group having between 1 and 4 carbon atoms; and $R_1$, $R_2$, and $R_3$ are independently selected from H, OH, F, Cl, Br, I, O—R (R is as defined above), or a substituted or unsubstituted lower alkyl group having between 1 and 4 carbon atoms (the alkyl group may be substituted with one or more hydroxyl or halide groups). For example, $R_1$ and $R_2$ may both be H while $R_3$ is —$CH_2$—Cl, —$CH_2$—Br, $CH_2$—I, or $CH_2$—OH.

In preferred embodiments, each of $R_1$, $R_2$, and $R_3$ are H. In other preferred embodiments, the compounds of Formula (VII) are acrylates including methyl, ethyl, propyl, and butyl acrylates.

In some embodiments, the reagent has the Formula (VIII),

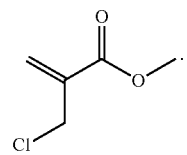

(VIII)

Examples of macromonomers of Formula (I) having a linker and a reagent include:

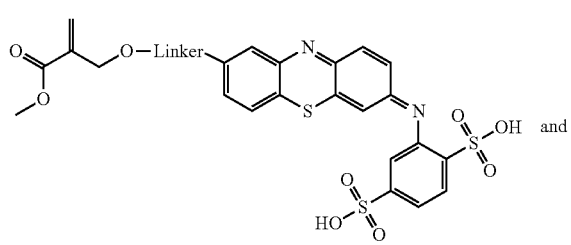

(IX)

and

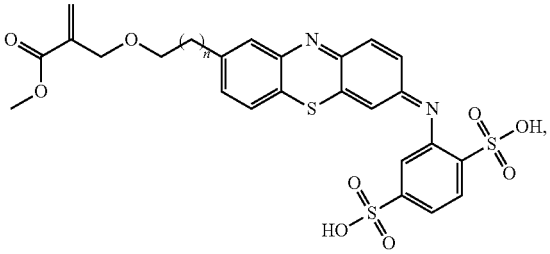

(IXa)

where n is an integer which ranges from 1 to 12.

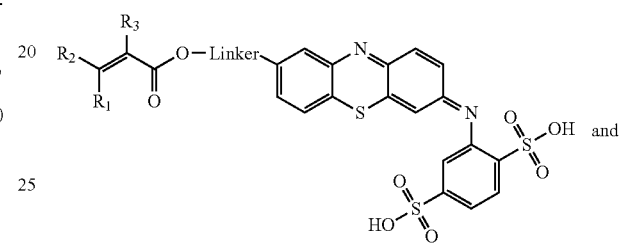

(X)

and

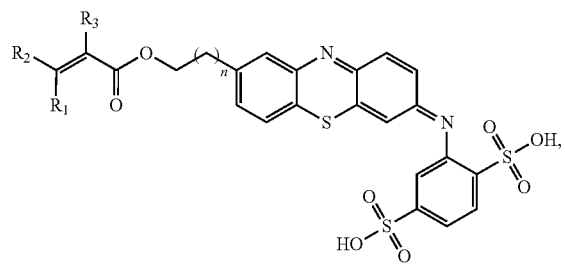

(Xa)

where n is an integer which ranges from 1 to 12.

Other reactive monomers (reagents) are also contemplated by the present invention, including azo compounds.

The macromonomers of Formulas (I) or (Ia) may be crosslinked or polymerized in the presence of an initiator, catalyst, heat, or UV-irradiation. The crosslinking or polymerization may be conducted in the presence of the biological molecules. Alternatively, the biological molecules may be introduced after crosslinking and/or polymerization.

Other crosslinking moieties may be added to assist in further crosslinking and/or polymerization.

The crosslinked or polymerized macromonomers may be end-capped, i.e. terminal reactive functional groups may be reacted with a moiety that slows or stops further crosslinking or polymerization. It is possible that "end-capping" may trap, bind, or react further quantities of biological molecules. Also, the size (molecular weight) of the polymers or copolymers may be controlled.

ADDITIONAL EMBODIMENTS

Example 1

A mixture of phenothiazine-monomer (e.g. Formulas (II) or (III)), initiator, cross-linkers (including PEG based cross-linkers) and other monomers for biocompatibility and enzyme immobilization could be directly polymerized on a transducer surface. This surface may first be initially modified to aid in the adhesion of the resulting polymer. The resulting polymer could be highly cross-linked or preferably a hydro-gel, which with the appropriately immobilized enzymes, could mediate the detection of glucose.

Example 2

Phenothiazine-monomer brushes could be grown from the surface of a transducer. One possible way this could be achieved is to immobilize an iniferter to the transducer, possibly through a silane coupling, and grow the brushes via UV-radiation. This could result in a high density of phenothiazine-derivative close to the sensor surface. The polymerization could also be done in the presence of enzyme immobilizing monomers, monomers and cross-linkers to alter the properties of the resulting brushes.

Example 3

The polymerizable macromonomers of Formula (I) could be polymerized into short poly(phenothiazine) chains. These chains could then be immobilized onto a sensor surface as recited above. The resulting polymer would be as in Example 1, except that the macromonomers would be immobilized in locally high concentrations. It is believed that this could aid electron transfer and mediation especially if these short poly(phenothiazine) chains were present in a high concentration relative to the cross-linkers.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A compound having the Formula:

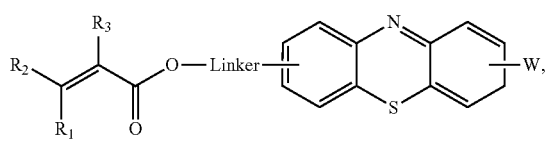

wherein

R$_1$, R$_2$, and R$_3$ are independently selected from the group consisting of H, OH, F, Cl, Br, I, O—R, and a substituted or unsubstituted lower alkyl group having between 1 and 4 carbon atoms, where said alkyl group may be substituted with one or more hydroxyl or halide groups;

R is H or a lower alkyl group having between 1 and 4 carbon atoms;

W is H or a moiety derived from the group having the formula

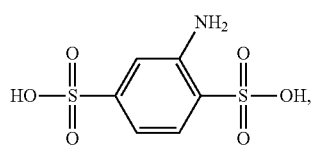 [SMILES: Nc1cc(S(=O)(=O)O)ccc1S(=O)(=O)O]

and

Linker is derived from polyethylene glycol or a substituted or unsubstituted aliphatic group having between about 2 and about 12 carbon atoms.

2. The compound of claim 1, wherein said compound has the Formula (X)

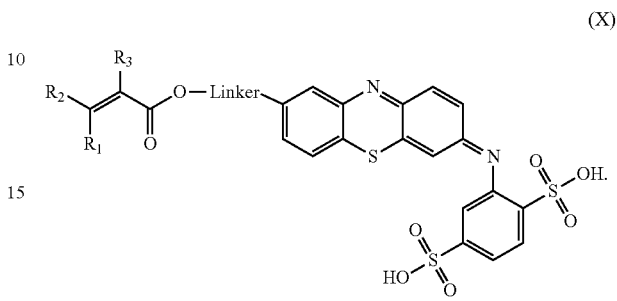

3. The compound of claim 1, wherein said compound has the Formula (Xa)

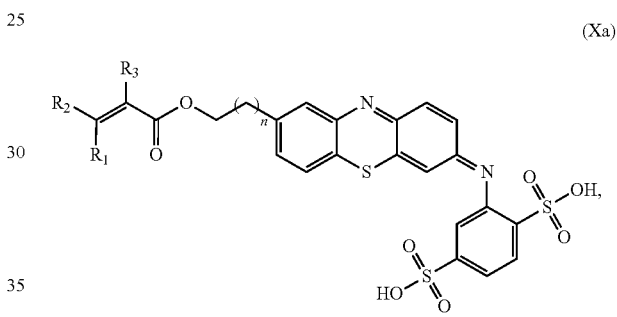

where n is an integer ranging from 1 to 12.

4. The compound of claim 1, wherein said Linker is derived from polyethylene glycol.

5. The compound of claim 1, wherein R$_1$, R$_2$, and R$_3$ are independently selected from H, methyl, ethyl, propyl, or butyl.

6. The compound of claim 1, wherein at least one of R$_1$, R$_2$, and R$_3$ is H.

7. A compound having the following formula:

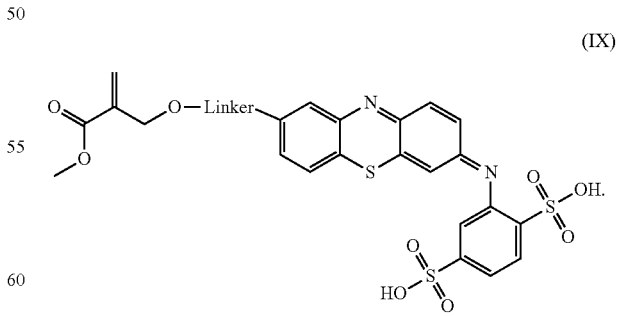

8. The compound of claim 7, wherein said Linker is derived from polyethylene glycol.

9. The compound of claim 7, wherein said compound has the Formula (IXa)

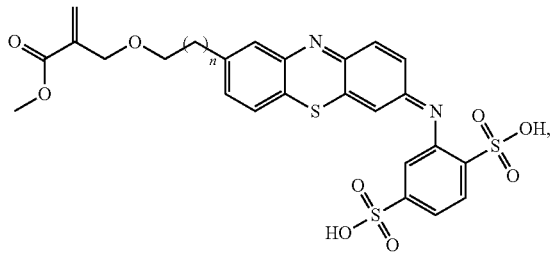

(IXa)

wherein n is an integer ranging from 1 to 12.

10. A polymer comprising at least one unit comprising the compound of claim 1.

11. A polymer comprising at least two units comprising the compound of claim 1.

12. The polymer of claim 10, wherein said polymer is crosslinked to a biological molecule.

13. The polymer of claim 10, wherein said polymer is crosslinked to a different polymer or copolymer.

14. A viscous solution comprising the polymer of claim 10 and a biological molecule.

15. The viscous solution of claim 14, wherein said biological molecule is an enzyme.

16. The viscous solution of claim 14, wherein said biological molecule is flavin adenine dinucleotide.

17. The viscous solution of claim 14, wherein said biological molecule is nicotinamide adenine dinucleotide.

18. The viscous solution of claim 14, wherein said biological molecule is trapped within a matrix of said polymer.

19. A film coating comprising the polymer of claim 10.

20. A medical device comprising a coating comprising the polymer of claim 10, wherein said coating is at least partially applied to at least one surface of said medical device.

21. The medical device of claim 20, wherein said medical device is a sensor, a transducer, or an electrode.

22. A method of polymerizing or crosslinking said compounds of claim 1, wherein said method comprises reacting at least two equivalents of the compounds of claim 1 in the presence of a catalyst to form a polymer, said catalyst selected from the group consisting of an initiator, heat, or UV-radiation.

23. The method of claim 22, wherein said crosslinking is performed in the presence of one or more biological molecules.

24. The method of claim 22, wherein said method further comprises the step of reacting said polymer with terminal reactive functional groups.

25. The method of claim 22, wherein said polymerization is performed on the surface of a medical device.

26. The method of claim 25, wherein said medical device is a sensor, a transducer, or an electrode.

* * * * *